(12) United States Patent
Wirostko

(10) Patent No.: US 9,782,345 B2
(45) Date of Patent: Oct. 10, 2017

(54) OCULAR COMPOSITION AND METHOD

(71) Applicant: Jade Therapeutics, Inc, Salt Lake City, UT (US)

(72) Inventor: Barbara Wirostko, Park City, UT (US)

(73) Assignee: Jade Therapeutics, Inc., Salt Lake City, UT (US)

( * ) Notice: Subject to any disclaimer, the term of this patent is extended or adjusted under 35 U.S.C. 154(b) by 0 days.

(21) Appl. No.: 14/584,787

(22) Filed: Dec. 29, 2014

(65) Prior Publication Data

US 2015/0157563 A1 Jun. 11, 2015

Related U.S. Application Data

(63) Continuation of application No. 14/517,041, filed on Oct. 17, 2014, now abandoned.

(60) Provisional application No. 61/892,436, filed on Oct. 17, 2013.

(51) Int. Cl.

| | |
|---|---|
| *A61K 9/00* | (2006.01) |
| *A61K 9/70* | (2006.01) |
| *A61K 31/4709* | (2006.01) |
| *A61K 45/06* | (2006.01) |
| *A61K 47/36* | (2006.01) |
| *A61K 31/407* | (2006.01) |
| *A61K 31/522* | (2006.01) |
| *A61K 31/5575* | (2006.01) |
| *A61K 31/7036* | (2006.01) |
| *A61K 38/14* | (2006.01) |

(52) U.S. Cl.
CPC .......... *A61K 9/0048* (2013.01); *A61K 9/0051* (2013.01); *A61K 9/7007* (2013.01); *A61K 31/407* (2013.01); *A61K 31/4709* (2013.01); *A61K 31/522* (2013.01); *A61K 31/5575* (2013.01); *A61K 31/7036* (2013.01); *A61K 38/14* (2013.01); *A61K 45/06* (2013.01); *A61K 47/36* (2013.01)

(58) Field of Classification Search
CPC ...... A61K 9/0048; A61K 38/14; A61K 47/36; A61K 9/0051
See application file for complete search history.

(56) References Cited

U.S. PATENT DOCUMENTS

| | | | |
|---|---|---|---|
| 5,660,851 A | 8/1997 | Domb | |
| 5,874,417 A | 2/1999 | Prestwich et al. | |
| 6,642,213 B1 | 11/2003 | Pastorello et al. | |
| 7,767,656 B2 | 8/2010 | Shoichet et al. | |
| 2002/0128512 A1 | 9/2002 | Bulpitt et al. | |
| 2004/0072793 A1 | 4/2004 | Aeschlimann et al. | |
| 2004/0192643 A1 | 9/2004 | Pressato et al. | |
| 2009/0082321 A1 | 3/2009 | Edelman et al. | |
| 2010/0015158 A1 | 1/2010 | Robinson et al. | |
| 2010/0028399 A1 | 2/2010 | Hornof | |
| 2010/0098772 A1 | 4/2010 | Robinson et al. | |
| 2010/0204325 A1 | 8/2010 | Blanda et al. | |
| 2011/0033540 A1 | 2/2011 | Daniloff et al. | |
| 2013/0136780 A1 | 5/2013 | Tezel et al. | |
| 2014/0023692 A1 | 1/2014 | Du Toit et al. | |
| 2014/0107025 A1 | 4/2014 | Wirostko | |
| 2014/0341842 A1* | 11/2014 | Zarembinski | A61K 47/36 424/85.1 |

FOREIGN PATENT DOCUMENTS

| | | |
|---|---|---|
| WO | WO 95/05803 | 3/1995 |
| WO | WO 2011/148116 | 12/2011 |
| WO | WO 2013/110056 | 7/2013 |
| WO | WO 2014/039012 | 3/2014 |

OTHER PUBLICATIONS

Allison et al, "Hyaluronan: A Powerful Tissue Engineering Tool", Biomaterials, 2006, pp. 2131-2140, vol. 12.
Bowe et al, "An in Vitro Study of the Potency and Stability of Fortified Ophthalmic Antibiotic Preparations", *Am J Ophthalmo*, 1991, pp. 686-689, vol. 111.
Camillieri et al, "Effects of Hyaluronan on Free-Radical Formation, Corneal Endothelium Damage, and Inflammation Parameters After Phacoemulsification in Rabbits", J Ocul Pharmacol Ther, 2004, pp. 151-157, vol. 720 No. 2.
Ciolino et al, "A Drug-Eluting Contact Lens", *Invest Ophthalmol Vis Sci*, 2009, pp. 3346-3352, vol. 50.
Ciolino et al, "A Prototype Antifungal Contact Lens", *Invest Ophthalmol Vis Sci*, 2011, pp. 6286-6291, vol. 52.
Granet et al, "A Multicenter Comparison of Polymyxin B Sulfate/Trimethoprim Ophthalmic Solution and Moxifloxacin in the Speed of Clinical Efficacy for the Treatment of Bacterial Conjunctivitis", *J Pediatr Ophthalmol Strabismus*, 2008, pp. 340-349, vol. 45.
Haas et al, "Monitoring Antibiotic Resistance in Ocular Microorganisms Results from the Antibiotic Resistance Monitoring in Ocular MicRorganisms (ARMOR), 2009 surveillance study", *Am J Ophthalmol*, 2011, pp. 567-574, vol. 152.
Higashide,"Use of Viscoelastic Substance in Ophthalmic Surgery—Focus on Sodium Hyaluronte", *Clin Ophthalmol*, 2008, pp. 21-30, vol. 2.

(Continued)

*Primary Examiner* — Gina Justice
(74) *Attorney, Agent, or Firm* — Burns & Levinson LLP; Joseph M. Maraia

(57) ABSTRACT

An ocular composition can include a polymer matrix and an antibiotic dispersed in the polymer matrix. The polymer matrix can contain a thiolated hyaluronic acid moiety cross-linked to a second moiety. The composition can be configured for placement in or on an eye of a subject to provide controlled release of the antibiotic to the eye. A method of treating or preventing an ocular disease can include providing an ocular composition and applying the ocular composition to a surface of an eye of a subject to provide controlled release of the antibiotic to the eye. The ocular composition can include a polymer matrix and an antibiotic dispersed in the polymer matrix. The polymer matrix can include a thiolated hyaluronic acid moiety cross-linked to a second moiety.

24 Claims, 5 Drawing Sheets

(56) References Cited

OTHER PUBLICATIONS

Hyatt et al, "Release of Vancomycin and Gentamicin from a Contact Lens Versus a Fibrin Coating Applied to a Contact Lens", *Invest Ophthalmol Vis Sci*, 2012, pp. 196-1952, vol. 53.

Inoue et al, "Improvement of Long-Term Prognosis in Patients with Ovarian Cancers by Adjuvant Sizofiran Immunotherapy: A Prospective Randomized Controlled Study", *Biotherapy* 1993, pp. 13-18, vol. 6.

Jain et al, "Development of Polyvinyl Alcohol-Gelatin Membranes for Antibiotic Delivery in the Eye", *Drug Dev Indusr Pharm*, 2011, pp. 167-177, vol. 37.

Kalwerisky et al, "Use of the Boston Ocular Surface Prosthesis in the Management of Severe Periorbital Thermal Injuries", *Ophthalmology*, 2012, pp. 516-521, vol. 119.

Keating, "Moxifloxacin 0.5% Ophthalmic Solution: In Bacterial Conjunctivitis", Drugs, 2011, pp. 89-99 vol. 71.

Koch et al, "A Comparison of Corneal Endothelial Changes After Use of Healon or Viscoat During Phacoemulsification", *Am J Ophthalmol*, 1993, pp. 188-201, vol. 115.

Laflamme et al, "A Comparative Study of Two Preservative-Free Tear Substitutes in the Management of Severe Dry Eye", *Can J Ophthalmol*, 1988, pp. 174-176, vol. 23.

Lawyer et al, "Formulation Changes Affect Material Properties and Cell Behavior in HA-Based Hydrogels", *Int J Cell Biol*, 2012, pp. 9, Article ID 737421.

Miller, "Review of Moxifloxacin Hydrochloride Ophthalmic Solution in the Treatment of Bacterial Eye Infections", Clin Ophthalmol, 2008, pp. 77-91, vol. 2, No. 1.

O'Brien et al, "Efficacy of Ofloxacin vs Cefazolin and Tobramycin in the Therapy for Bacterial Keratitis, Report from the Bacterial Keratitis Study Research Group", Arch Ophthalmol, 1995, pp. 1257-1265, vol. 113, No. 10.

Polack, "Penetrating Keratoplasty Using MK Stored Corneas and Na Hyaluronate (Healon)", *Trans Am Ophthalmol Soc*, 1982, pp. 248-261, vol. 80.

Prestwich et al, "Chemically-Modified HA for Therapy and Regenerative Medicine", *Curr Pharm Biotechnol*, 2008, pp. 242-245, vol. 9.

Rah, "A Review of Hyaluronan and its Ophthalmic Applications", *Optometry*, 2011, pp. 38-43, vol. 82.

Robertson et al, "Ocular Pharmacokinetics of Moxifloxacin After Topical Treatment of Animals and Humans",*Surv Ophthalmol*, 2005, pp. S32-S45, vol. 50, Suppl 1.

Sand et al, "Sodium Hyaluronate in the Treatment of Keratoconjunctivitis Sicca, A Double Masked Clinical Trial", *Acta Ophthalmol*, 1989, pp. 181-183, vol. 67, Copenhagen, Denmark.

Sharma et al, "Evaluation of Moxifloxacin 0.5% in Treatment of Nonperforated Bacterial Corneal Ulcers: A Randomized Controlled Trial", Ophthalmology, 2013, pp. 1173-1178, vol. 120, No. 6.

Silver et al, "Clinical Safety of Moxifloxacin Ophthalmic Solution 0.5% (VIGAMOX) in Pediatric and Nonpediatric Patients with Bacterial Conjunctivitis", *Surv Ophthalmol*, 2005, pp. S55-S63, vol. 50, Suppl 1.

Tian et al, "Studies on the Uptake and Release of Fluoroquinolones by Disposable Contact Lenses", *CLAO J*, 2001, pp. 216-220, vol. 27.

Vanderhooft et al, "Rheological Properties of Crosslinked Hyaluronan-Gelatin Hydrogels for Tissue Engineering", *Macromol Biosci*, 2009, pp. 20-28, vol. 9.

Volker-Dieben et al, "A Double-Blind, Randomized Study of Healon GV Compared with Healon in Penetrating Keratoplasty", *Cornea*, 1994, pp. 414-417, vol. 13.

Zarembinki et al, "Thiolated Hyaluronan-based Hydrogels Crosslinked Using Oxidized Glutathione: An Injectable Matrix Designed for Ophthalmic Applications", Acta Biomaterialia, Jan. 2014, pp. 94-103, vol. 10, Issue 1, BioTime Inc, Alameda, CA.

\* cited by examiner

OCULAR COMPOSITION AND METHOD

RELATED APPLICATIONS

This application claims the benefit of U.S. application Ser. No. 14/517,041 filed Oct. 17, 2014 which claims priority to U.S. Provisional Application No. 61/892,436, filed Oct. 17, 2013, which are both incorporated herein by reference.

BACKGROUND

Corneal ulcers are an ocular emergency and a leading cause of blindness globally. It is estimated that corneal opacities, including those secondary to corneal ulceration due to infections, are the fourth leading cause of blindness worldwide. The annual occurrence of corneal ulcers is roughly 1.5 to 2 million globally, with studies indicating that greater than half of the U.S. cases are due to bacteria. Common pathogens causing corneal ulcers include *Staphylococcus aureus, Streptococcus pneumonia, Neisseria gonorrhoeae, Hemophilus influenza*, and *Pseudomonas aeruginosa*. Bacterial corneal ulcers can result from inappropriate contact lens wear, trauma, and persistent corneal epithelial defects secondary to severe dry eye, neurotrophic/diabetic keratitis, and chemical damage such as chemical exposure that can occur in a military theater. Corneal ulcers can also be caused by fungi, viruses, and protozoa. In developing countries, many children with Vitamin-A deficiency are at high risk for corneal ulcers and may become permanently blind as a result.

Treatment of corneal ulcers can include antibiotics, antifungals, antivirals, and other therapeutic agents. In some cases, treatment requires applying topical medications according to an inconvenient hourly round-the-clock schedule, which may continue for multiple days. In some cases, superficial corneal ulcers can heal in less than a week. However, deeper ulcers can take longer to heal and may require additional treatments. Failure to comply with a treatment schedule can result in ineffective drug exposure, superinfections, resistant pathogens, progression of the disease, and visual degradation.

SUMMARY

The present technology provides ocular compositions and methods of treating or preventing an ocular disease such as corneal ulcers using ocular compositions. In one aspect, an ocular composition can include a polymer matrix and an antibiotic dispersed in the polymer matrix. The polymer matrix can be formed from a thiolated hyaluronic acid moiety cross-linked to a second moiety. This composition can be configured for placement in or on an eye of a subject, and the composition can provide a controlled release of the antibiotic to the eye.

In another aspect, a method of treating or preventing an ocular disease can include providing an ocular composition and applying the ocular composition to a surface of an eye of a subject to provide controlled release of the antibiotic to the eye. The ocular composition can include a polymer matrix and an antibiotic dispersed in the polymer matrix. The polymer matrix can be formed from a thiolated hyaluronic acid moiety cross-linked to a second moiety.

Other features of the present technology will become clearer from the following detailed description of the invention, taken with the accompanying drawings and claims, or may be learned by the practice of the invention.

BRIEF DESCRIPTION OF THE DRAWINGS

For a further understanding of the nature and advantage of the present disclosure, reference is being made to the following detailed description of embodiments and in connection with the accompanying drawings, in which.

DETAILED DESCRIPTION

Figure 1:
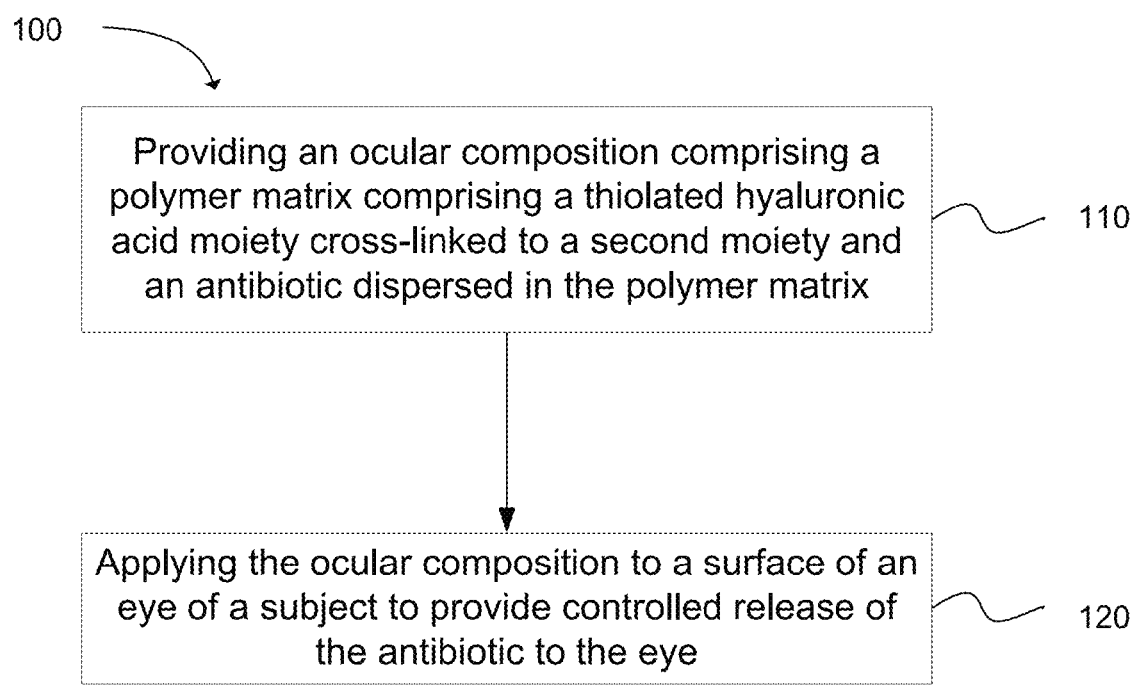
FIG. 1 is a flowchart of a method of treating or preventing an ocular disease in accordance with an embodiment of the present disclosure.

In describing embodiments of the present invention, the following terminology will be used.

The singular forms "a," "an," and "the" include plural referents unless the context clearly dictates otherwise. Thus, for example, reference to "an active agent" includes reference to one or more of such pellets and "dispersing" includes one or more of such steps.

As used herein, the term "subject" refers to a mammal Non-limiting examples of mammals can include rats, mice, dogs, cats, rabbits, horses, non-human primates, and humans. In one preferred aspect, the subject is a human.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained.

As used herein, a plurality of items, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "50-250 micrograms" should be interpreted to include not only the explicitly recited values of about 50 micrograms and 250 micrograms, but also to include individual values and sub-ranges within the indicated range. Thus, included in this numerical range are individual values such as 60, 70, and 80 micrograms, and sub-ranges such as from 50-100 micrograms, from 100-200, and from 100-250 micrograms, etc. This same principle applies to ranges reciting only one numerical value and should apply regardless of the breadth of the range or the characteristics being described.

As used herein, the term "about" means that dimensions, amounts, formulations, parameters, and other quantities and characteristics are not and need not be exact, but may be approximated and/or larger or smaller, as desired, reflecting tolerances, conversion factors, rounding off, measurement error and the like and other factors known to those of skill. Further, unless otherwise stated, the term "about" shall expressly include "exactly," consistent with the discussion above regarding ranges and numerical data.

As used herein, the term "small molecule therapeutic agent" refers to a compound having a molecular mass of 2000 or less. In a specific definition, the compound has a molecular mass of 1500 or less. In another specific definition, the compound has a molecular mass of 1000 or less. In yet another specific definition, the compound has a molecular mass of 750 or less. In again yet another specific definition, the compound has a molecular mass of 500 or less.

As used herein, the term "antimicrobial" refers to an antifungal agent, an antibiotic agent or an antiviral agent.

As used herein, the term "moiety" refers to a component of a polymer matrix used in an ocular composition. A moiety can be a functional group, a molecule, a monomer, a group of linked monomers, a polymer chain, and so on. For example, in one specific embodiment, the polymer matrix can comprise thiolated carboxymethyl hyaluronic acid moiety cross-linked to a poly(ethylene glycol) diacrylate moiety. The thiolated carboxymethyl hyaluronic acid moiety can comprise polymer chains of thiolated carboxymethyl hyaluronic acid. The poly(ethylene glycol) diacrylate moiety can comprise poly(ethylene glycol) diacrylate polymer chains.

As described herein, an ocular composition is provided for placement in, around, or on an eye of a subject (e.g., mammalian or human) is provided. The ocular composition provides controlled release of an amount of a small molecule therapeutic agent to the eye effective to treat or prevent a disease or condition of the eye. The ocular composition has a small molecule therapeutic agent and a polymeric matrix. In one specific aspect, the small molecule therapeutic agent can be an antibiotic. In a further specific aspect, the ocular composition can include an antibiotic as well as an additional small molecule therapeutic agent. In another specific aspect, the composition can be a topical solution or gel, emulsion, ointment, insert or film. The ocular composition can be inserted, applied topically, sprayed or injected to a desired ocular region. Thus, the ocular composition is configured for placement in the eye of a subject, and provides controlled release of an effective amount of the active agent to the eye. The ocular composition can be configured as a daily sustained release topical formulation, sustained-release topical formulation, injection, spray, gel, ointment, depot, film or the like. In one particular embodiment, the ocular composition can be a film configured to be applied to a surface of the eye.

In further aspects, the ocular composition can be a microparticle suspension, a nanoparticle suspension, a monolithic rod, film, a sponge, or a gel. In some aspects, the ocular composition is shaped for application to an ocular region which subconjunctival, sub-Tenons, cul de sac, conjunctiva, on the cornea, limbus, intra corneal, periocular region, sub-Tenon's space, subscleral, peribulbar or retrobulbar. In another aspect, the ocular composition is a depot or film placed under the eyelid. Further, the composition can be injectable or insertable. The polymer matrix having the small molecule therapeutic agent as described herein can be delivered directly to the target tissue or placed in a suitable delivery composition (e.g., a ophthalmically acceptable carrier) for delivery of the ocular composition to a target ocular region or tissue.

The ocular composition described herein can provide controlled release of the small molecule therapeutic agent to an ocular tissue or region for an extended duration, e.g. from several hours to about 200 days. Release of the active agent can further exhibit zero-order release kinetics for substantially the entire release duration with a tapering off as the drug substantially completes release. The controlled release can also exhibit near zero order kinetics for substantially the entire release duration and can optionally be delivered with or without an initial burst. The amount of small molecule therapeutic agent released by the ocular composition can include an initial bolus followed by zero-order and or single-order kinetic release for substantially the remainder of duration of treatment. Release modes provided include burst, continuous release and or pulsed release. In another aspect, the concentration of the active agent in the matrix is from about 0.05 µg to about 500 µg per milliliter.

The polymer matrix of the delivery composition can include a bioerodible polymer that erodes to provide a rate of controlled release. In one embodiment, the polymer matrix can include a thiolated hyaluronic acid moiety cross-linked to a second moiety. For example, in one specific embodiment, the polymer matrix can comprise thiolated carboxymethyl hyaluronic acid moiety cross-linked to a poly(ethylene glycol) diacrylate moiety. In a specific embodiment, the thiolated hyaluronic acid can be Glycosil® hyaluronic acid. Glycosil is a component of HyStem®, HyStem-C and HyStem-HP hydrogel kits available from BioTime, Inc. Glycosil is also available separately in individual vials.

The polymer matrix can optionally include additional bioerodible polymers. Such bioerodible polymers can include, without limitation, polyester amides, amino acid based polymers, polyester ureas, polythioesters, polyesterurethanes, collagen based polymers, and copolymers and mixtures thereof. In one embodiment, the bioerodible polymer exhibits an amino acid polymerized via hydrolytically labile bonds at a side chain of the amino acid. In another embodiment, the polymer is a polymerization product of at least one of glycolic acid, glycolide, lactic acid, lactide, e-caprolactone, p-dioxane, p-diozanone, trimethlyenecarbonate, bischloroformate, ethylene glycol, bis(p-carboxyphenoxy) propane, and sebacic acid. In one aspect, glycolic acid and lactic acid are present in a ratio selected to provide a rate of controlled release.

The small molecule therapeutic agent can be dispersed in the polymer matrix as a solid, a powder, a gel, a solution, microparticles, or emulsion. The ocular composition includes a small molecule therapeutic agent, including, but not limited to, an antibiotic, an antimicrobial agent (including an antivirals or antifungal), or any combination thereof. In a particular embodiment, the ocular composition is situated adjacent to a rate controlling diffusion barrier.

A method of making an ocular composition includes dispersing a small molecule therapeutic agent in a polymer matrix selected to provide controlled release of an amount of the small molecule therapeutic agent to the eye. In one specific aspect, the polymer matrix is cross-linked and the small molecule therapeutic agent is dispersed in the polymer matrix prior to cross-linking of the polymer matrix. In another specific aspect, the polymer matrix is cross-linked and the small molecule therapeutic agent is dispersed in the cross-linked polymer matrix (e.g., subsequent to cross-linking of the polymer matrix).

A method of promoting ocular health in a subject includes placing an ocular composition in an eye of the subject. The ocular composition includes a small molecule therapeutic dispersed in a polymer matrix that provides continuous controlled release of an effective amount of the small molecule therapeutic agent to one or more ocular regions or tissues. In a particular embodiment, placement is subconjunctivally. In another particular embodiment, the placement is in or near the limbus, periocular region, sub-Tenon's space, subsclera, subcorneal or the retrobulbar space. In a particular example, placement of the ocular composition is by injection. In another embodiment, the composition is placed under or within a contact lens (e.g., collagen or other dissolvable matrix, or absorbable suture material like a cross-linked hyaluronic acid polymer e.g., see the examples (or e.g., Poly lactic glycolic acid (PLGA) and polylactic acid (PLA)) or other silicone based matrix). In still another embodiment a signal can be applied to the ocular composition after placement to initiate to alter the controlled release. The signal may be a remote signal. In a particular example, the controlled release occurs via iontophoresis.

In some embodiments of the present technology, the ocular composition can comprise an antibiotic dispersed in a polymer matrix. For example, the antibiotic can be selected from aminoglycosides, penicillins, cephalosporins, fluoroquinolones, macrolides, and combinations thereof. Exemplary aminoglycosides that can be used include, but are not limited to: tobramycin, kanamycin A, amikacin, dibekacin, gentamicin, sisomicin, netilmicin, neomycin B, neomycin C, neomycin E, streptomycin, paramomycin, and combinations thereof. Exemplary penicillins that can be used include, but are not limited to: amoxicillin, ampicillin, bacampicillin, carbenicillin, cloxacillin, dicloxacillin, flucloxacillin, mezlocillin, nafcillin, oxacillin, penicillin G, penicillin V, piperacillin, pivampicillin, pivmecillinam, ticarcillin, and combinations thereof. Exemplary cephalosporins that can be used include, but are not limited to: cefacetrile, cefadroxil, cefalexin, cefaloglycin, cefalonium, cefaloridine, cefalotin, cefapirin, cefatrizine, cefazaflur, cefazedone, cefazolin, cefradine, cefroxadine, ceftezole, cefaclor, cefamandole, cefmetazole, cefonicid, cefotetan, cefoxitin, cefprozil, cefuroxime, cefuzonam, cefcapene, cefdaloxime, cefdinir, cefditoren, cefetamet, cefixime, cefmenoxime, cefodizime, cefotaxime, cefpimizole, cefpodoxime, cefteram, ceftibuten, ceftiofur, ceftiolene, ceftizoxime, ceftriaxone, cefoperazone, ceftazidime, cefclidine, cefepime, cefluprenam, cefoselis, cefozopran, cefpirome, cefquinome, ceftobiprole, ceftaroline, cefaclomezine, cefaloram, cefaparole, cefcanel, cefedrolor, cefempidone, cefetrizole, cefivitril, cefmatilen, cefmepidium, cefovecin, cefoxazole, cefrotil, cefsumide, cefuracetime, ceftioxide, and combinations thereof. Exemplary fluoroquinolones that can be used include, but are not limited to: ciprofloxacin, levofloxacin, gatifloxacin, moxifloxacin, ofloxacin, norfloxacin, and combinations thereof. Exemplary macrolides that can be used include, but are not limited to: azithromycin, erythromycin, clarithromycin, dirithromycin, oxithromycin, telithromycin, and combinations thereof. Other exemplary antibiotics that can be used include, but are not limited to: bramycin, besifloxacin, levofloxacin, polymyxin B combinations such as polymyxin B/trimethoprim, polymyxin B/bacitracin, polymyxin B/neomycin/gramicidin, and the like.

In some aspects, the ocular composition can also include additional small molecule therapeutics. In one aspect, the small molecule therapeutic is ketorolac, naphazoline, lidocaine, pemirolast, brimonidine, bepotastine, cysteamine, difluprednate, bimatoprost, dexamethasone, unoprostone isopropyl, travoprost, valganciclovir, cidofovir, verteporfin, tafluprost, ganciclovir, or a combination thereof.

In one aspect, when used in connection with hyaluronic acid-based polymers, the ocular composition described herein is useful for an ocular disease or indication such as post-surgical inflammation, anesthesia, open-angle glaucoma, ocular hypertension, allergic conjunctivitis, seasonal or perennial allergic rhinitis, bacterial conjunctivitis, itching associated with allergic conjunctivitis, lowering IOP, glaucoma, corneal cystine crystal accumulation due to cystinosis, inflammation, pain, corneal ulcers, macular edema following branch retinal vein occlusion or central retinal vein occlusion, low tear production, cytomegalovirus retinitis in patients with AIDS, inflammation of the cornea due to herpes simplex virus and/or a fungus, cytomegalovirus (CMV) retinitis, wet age-related macular degeneration (wet AMD), or acute herpetic keratitis.

Small molecule therapeutic agents that are useful for treating or preventing an ocular disease or indication can be used in the ocular compositions as described herein. Small molecule therapeutic agents can offer major potential benefit for patients with a variety of ocular diseases and indications such as surgical and non-surgical trauma, refractive interventions, corneal abrasion, corneal ulcers, neurotrophic corneas secondary to diabetes, trauma, surgery, cranial nerve palsies, infectious keratitis, bacterial conjunctivitis and/or corneal ulcers.

Accordingly, in one aspect an ocular composition is provided comprising a composition having a small molecule therapeutic agent in a subject, where the small molecule therapeutic agent is dispersed in a pharmaceutical carrier in a polymer matrix. Furthermore, the ocular composition is configured for placement in or on an eye of a subject, and provides controlled release of an amount of the small molecule therapeutic agent to the eye effective to treat or prevent an ocular disease or indication.

Thus, the ocular composition described herein is useful in particular for treating or preventing an ocular disease or indication. Improvements of a disease or indication of the eye, through the mechanism of application a composition having small molecule therapeutic agent in a polymer matrix, can remarkably or significantly improve the eye and recurrence of the disease or indication. Furthermore, a composition having a small molecule therapeutic agent in a cross-linked hyaluronic acid polymer can continuously release the therapeutic agent to the eye. An active agent such as a small molecule therapeutic agent can be delivered to an eye of a subject via a variety of mechanisms and delivery modalities, both invasive and non-invasive. For example, in one aspect the small molecule therapeutic agent is delivered to the eye in a topical form. Topical delivery can be in a frequently applied manner and/or in a sustained release manner that can facilitate improvements in an ocular disease or indication.

The use of a small molecule therapeutic agent in a sustained (or controlled) release delivery mode can also allow for improved patient compliance and adherence. Daily topical and/or sustained (or controlled) application of a small molecule therapeutic agent can also improve treatment outcomes.

As has been described, delivery of a small molecule therapeutic agent to the eye can be accomplished via non-invasive or invasive techniques. An invasive technique is defined herein as an ocular delivery technique whereby an ocular membrane or tissue is physically disrupted during active agent delivery, or placement of an active agent depot. For example, injections, implantations, and the like are considered to be invasive because ocular tissue is disrupted by a needle or other surgical instrument during delivery. In topical delivery, on the other hand, an active agent is placed on a tissue surface of the eye and passively delivered there through. It should be noted that, the type of disruption caused by an electrical field such as by electroporation or iontophoresis would be considered to be a non-invasive delivery as such techniques generally do not physically disrupt ocular membranes and tissue. Microneedle delivery, on the other hand, would be considered to be an invasive technique.

The present technology is thus directed to an ocular composition for sustained delivery of a small molecule therapeutic agent and other beneficial compounds to the eye of a subject. In one specific aspect, an ocular composition comprises a formulation including a small molecule therapeutic agent dispersed in a polymer matrix and configured for placement in, on and or around the eye of a subject. In one aspect, the small molecule therapeutic agent is an antibiotic. In a particular aspect, the polymer matrix with the small molecule therapeutic agent dispersed therein provides controlled release of an amount of the small molecule therapeutic agent to the eye effective to treat or prevent an ocular disease or indication.

The delivery approach according to aspects of the present disclosure enables a system including a drug-and-polymer depot to be placed in contact with tissues of the eye such that the small molecule therapeutic agent is released to the surface of the eye in a continuous or pulsatile manner, or is released into the eye at an internal location in a continuous or pulsatile manner. As used herein, the term "depot" refers to a collection of material that includes a small molecule therapeutic agent and that can be placed in an area of interest to provide sustained release of the small molecule therapeutic agent at least to that area. Accordingly, a method of promoting treatment or prevention of an ocular disease or indication in a subject can include placing a small molecule therapeutic agent delivery depot as described herein in an eye of the subject. The composition can be placed in a variety of locations on or in the eye, and any such location is considered to be within the present scope. In one aspect, for example, a depot can be placed adjacent to a surface of the cornea, conjunctiva, and or sclera. Placement of the depot can also be on or within the sclera (episcleral); beneath or within overlying tissues such as the subconjunctival tissue, e.g. at or near the limbus; the periocular region; within the sub-Tenon's space; and in posterior retrobulbar locations.

The time, rate, and efficiency of the processes of delivery of the small molecule therapeutic from the ocular composition to the target tissues is controlled to maintain at least a minimum titer small molecule therapeutic agent over the desired period. Drug delivery duration will depend upon the severity and underlying process being treated. In one aspect, the composition and location of the composition can be selected to allow the controlled and sustained release of a small molecule therapeutic agent to occur over a span of from several hours to several months. In a specific example, the depot provides controlled release for a period from about 2 days to about 200 days. In another aspect, the controlled release has a duration of from about 1 hour to about 200 days. In yet another aspect, the controlled release has a duration of from about 1 day to about 3 days. In yet another aspect, the drug-polymer depot can be configured to provide continuous release having zero-order kinetics over substantially the entire release duration.

Release by the composition provides a dose of a small molecule therapeutic agent to the eye in which it is placed. In one embodiment, the small molecule therapeutic agent is released in a continuous fashion for a particular duration. In alternative embodiment, the composition provides release of a small molecule therapeutic agent in a pulsatile fashion, i.e. two or more discrete doses of a given duration and amount and separated by an interval of time. The timing of the pulses can be according to a single fundamental frequency, or can exhibit a more complex temporal pattern. This allows for an additional level of control of release, e.g. to promote greater efficacy or address safety issues. For example, intermittent release can reduce potential adverse effects of constant stimulation.

Controlled release by the composition provides to the eye a dose of a small molecule therapeutic agent that is effective to treat or prevent an ocular disease or indication. In one embodiment, the composition is configured to release a particular amount of a small molecule therapeutic agent per day. An effective amount of a small molecule therapeutic agent may depend on the exact type of agent and disease or indication. Other possible factors include the age, weight, and medical history of the subject. Accordingly, the composition can be configured to provide a proper dose based on these or other factors. In another example, release of a small molecule therapeutic agent can be upwards of 250 mg for a 60 day delivery. In another example, the concentration of small molecule therapeutic agent included in the composition polymer material is from about 0.01 µg/ml to about 500 µg/ml. In one aspect, the amount of a small molecule therapeutic agent provides a concentration of about 0.01% to about 0.5% small molecule therapeutic agent in a 30-50 µl eye drop administered QID (4×/day). In still another aspect, 100 ug/ml can be topically delivered in a 30-50 µl dose 4×/day to treat or prevent an ocular disease or indication. For example, a 12 µg loading dose can release 4-6 µg upon placement with 1-2 µg/day thereafter for up to 1 week. In another aspect, the total daily concentration of a small molecule therapeutic agent provided is from about 0.2% to about 10.0% or 0.5 µg to 50 µg/day.

In one aspect, a small molecule therapeutic agent is combined with a polymer matrix, and an amount of this combination is used to create a drug-polymer composition that provides controlled release of a small molecule therapeutic agent. The physical properties of the composition can be selected to be suitable for different modes of placement, e.g. topical application on the surface of the eye or subconjunctival, sub-Tenon's, peribulbar placement. The drug-polymer composition can comprise a microparticle or nanoparticle suspension, a solid or semi-rigid monolithic rod, film or a gel. In one embodiment, the polymer matrix can be sufficiently liquid to be administered as eye drops and then allowed to gel on the surface. In another aspect, the polymer matrix can be injected into an ocular space such as the subconjunctival, suprachoroidal space as a liquid and or gel. In still another aspect, the drug-polymer matrix can be applied to a structure that is then placed on an ocular surface in the cul de sac and or on the cornea. With such approaches, the polymer matrix can be selected to be flowable while exhibiting sufficient cohesiveness so that it is not easily diluted or washed away from the placement site. In another embodiment, the polymer matrix can be selected to form a more solid structure shaped for placement on or under an ocular surface.

In a particular embodiment, the polymer matrix can be formed into a film for placement on a surface of the eye. The film can be a solid film with any suitable shape for placement on a surface of the eye. For example, the film can be square shaped, circular, ellipsoid, or any other suitable shape. In some cases, the film can be a circular film with a diameter from about 2 mm to about 20 mm. In other cases, the film can be a circular film with a diameter from about 5 mm to about 7 mm. In one specific case, the film can be a circular film with a diameter of about 6 mm. These diameters can be diameters of the film when dry or when hydrated. The film can also have a suitable thickness and curvature for being placed on the surface of the eye. For example, the film can have a thickness from about 0.05 mm to about 3 mm. In other examples, the film can have a thickness from about 0.1 mm to about 2 mm. These thicknesses can be dry or hydrated thicknesses. The films may be a strip about 2-6 mm in width and up to 20 mm in length. The films may have a flat and or rounded/curved surface allowing adherence and or movement against the surface. The ends may be rounded and or tapered and one surface may be irregular and or altered to reduce friction and movement on the ocular surface. The films may also range from upper fornix to lower fornix hence covering the majority of the ocular surface.

Generally, a dry film can swell when placed on the surface of the eye due to the film becoming hydrated by tears or other fluids in the eye. In some embodiments, the film can be provided as a dried film which is applied to the surface of the eye and then allowed to swell. Depending on the degree of hydration, a dried film can swell from a dry volume to a hydrated volume that is from 200% to 800% of the dry volume. In further examples, the film can swell to a hydrated volume that is from about 300% to 600% of the dry volume.

The polymer matrix can be formed into a film by any suitable method. In certain embodiments, the film can be formed by spreading a mixture of cross-linkable moieties on a surface to a desired film thickness, and allowing the cross-linkable moieties to cross-link, thus forming the polymer matrix. Alternatively, a mold can be used in the desired shape of the film. The cross-linking can be allowed to continue for a sufficient time to from a cross-linked polymer matrix. In some cases, the cross-linking time can be from about 10 minutes to about 10 hours, from about 1 hour to about 5 hours, or from about 2 hours to about 4 hours. The polymer matrix can be hydrated with water when formed. After formation of the film, the film can be used in its hydrated state or dried. In one example, the film can be dried in an oven to form a dry film. Drying time can be sufficient to reduce the water content in the film to substantially little or no water, less than 5 wt % water, less than 10 wt % water, or less than 20 wt % water. Drying time can depend on the temperature and humidity used during drying, but in many cases the drying time can be from about 2 hours to about 30 hours, from about 5 hours to about 25 hours, or from about 10 hours to about 20 hours. After drying, the dried film can be applied to the surface of the eye and allowed to rehydrate on the surface of the eye. The dried film can be applied in the shape in which the film was formed, or the dried film can alternatively be cut into a different shape before application. In one embodiment, a large dried film can be formed and then multiple smaller films can be cut from the large dried film using a suitable cutting tool such as a knife, a die, a hole punch, and so on.

In a particular embodiment, the composition can comprise polymers that are bioerodible, so that the composition is gradually broken down over time rather than needing to be removed at the end of a treatment period. As used herein, "bioerodible" refers to the ability of a material to be broken down by processes in a physiological environment, and rendered into smaller units that can be dealt with by the body. In particular this can refer to rendering the material water-soluble and further resorbable by the body. In one embodiment, controlled release of the active agents from the composition is accomplished by the degradation of bioerodible biopolymers included in the polymer matrix.

In an embodiment, the polymer matrix can include a hyaluronic acid polymer, optionally with an additional bioresorbable polymer or mixture of polymers that is compatible with placement in the eye and that can provide the desired release profile. These can include without limitation, hyaluronic acid, polyester amides, amino acid based polymers, polyester ureas, polythioesters, polyesterurethanes, and the like, including copolymers and mixtures thereof. In a particular example, bioresorbable polyesters derived from lactone-based biocompatible monomers (glycolic acid, glycolide, lactic acid, lactide, e-caprolactone, p-dioxane and trimethlyenecarbonate) can be used. In another aspect, the polymer is a chitosan oligosaccharide based polymer. Other possible monomers include bischloroformate, ethylene glycol, bis(p-carboxyphenoxy) propane, sebacic acid, p-diozanone, and the like. Additionally, in one aspect the bioerodible polymer can include a moiety derived from thiolated carboxymethyl hyaluronic acid and a moiety derived from poly(ethylene glycol) diacrylate. In another aspect, the bioerodible polymer can include an amino acid polymerized via hydrolytically labile bonds at a side chain of the amino acid.

In a specific embodiment, a bioerodible polymeric composition can comprise a plurality of monomer units of two or three amino acids which are polymerized via hydrolytically labile bonds at their respective side chains rather than at the amino or carboxylic acid terminals by amide bonds. Such polymers are useful for controlled release applications in vivo and in vitro for delivery of a wide variety of biologically and pharmacologically active ligands. According to another embodiment, the polymer matrix can include bioerodible polymers such as polylactic glycolic acid based polymers. Such PLGA polymers can be modified by polycondensation and multiblock copolymers—bischlorofomates, polyethyleneglycol, and poly-ϵ-caprolactone. In particular, dissolution times in aqueous media and in tissue can be tuned within an ample range, from a few days to several months. This provides fine tuning of the polymer device in view of specific applications of delivering biologics in the periocular space and region. In the case of multiblock polymers, the nature and the length of the starting diol can be varied to provide the release characteristics such as described above.

Bioerodible ortho ester polymers can also be used for preparing solid form bioerodible pharmaceutical compositions such as pellets, capsules, and rods that can be utilized to contain the active agent. In a specific example, a bioerodible polyanhydride composed of bis(p-carboxyphenoxy) propane and sebacic acid can also be used as the drug carrier for periocular and subconjunctival drug delivery.

Hyaluronic acid is a nonlinear polysaccharide that that is naturally occurring in ocular tissue in sizes that range from 100 kDa to 8000 kDa. It is a naturally occurring component of the extracellular matrix and the vitreous body and can be used as a therapeutic to help wounds heal, provide structural support, and deliver drugs and/or proteins. With chemical modifications, cross linking can alter its physical properties thus enabling it to be more viscous and or gel like. It can be used to deliver various small molecule therapeutic agents to the ocular tissues in a variety of applications using the drug delivery systems herein.

Additionally, in some aspects additional ingredients can be added to the bioerodible polymer to improve a variety of polymeric properties such as mucoadhesiveness, flexibility, and the like. Non-limiting examples of such ingredients can include methylcellulose, carboxymethylcellulose, hydroxypropyl methylcellulose, hydroxyethyl cellulose, ethylcellulose, hydroxyethylcellulose, hydroxylpropyl cellulose, polyvinyl alcohol, polyvinyl-pyrrolidone, alginic acid, chitosan, xanthan gum, carrageenan, poly(acrylic) acid, or a derivative thereof.

In accordance with the present disclosure, a drug delivery system can utilize other mechanisms for controlled release of active agent formulation. For example, the drug-polymer matrix can be substantially contained in a space under a structure on the ocular surface, such as a contact lens or bandage lens. The composition may be applied to the underside of the contact lens before insertion in the eye, or alternatively the composition can be applied to the cornea or sclera and subsequently covered by the lens.

In another embodiment, the system can include a structure to mediate release of the formulation to the eye. In a particular example, the composition can be placed adjacent to a rate controlling diffusion barrier that comprises diffusion control materials, e.g. in a subconjunctival implant. In another example of an implant, release can be aided or accomplished by iontophoresis. The implant can include a membrane or barrier having transport properties that are modulated by changing the electrical state of the barrier. Non-limiting examples of electrically inducible mechanisms for drug release include ion exchange and electroporation. Iontophoretic release can be controlled by application of a signal to the drug delivery system. Such a control signal, e.g. an electrical signal, can be applied directly to the implant, or alternatively can be conveyed by a remote signaling device. To accommodate this type of control, the implant can further include a device, e.g. a microchip, configured to receive and transmit a signal to the barrier that is appropriate to modify the electrical state of the barrier. Additionally, it is also contemplated that an implant can utilize an expanding hydrogel to deliver the active agent from the implant reservoir.

Generally, the ocular composition can contain an antibiotic dispersed in the polymer matrix. Additionally, the ocular composition can optionally contain other suitable active agents. In some embodiments, these secondary active agents can be therapeutic agents that promote eye function.

Suitable small molecule therapeutic agents for inclusion can include by way of example:

Additional antibiotics such as ciprofloxacin, gatifloxicin, moxifloxacin, bacitracin, tobramycin, vancomycin, macrolides, polymyxin, gramidicin, erythromycin, tetracycline, azithromycin, erythromycin, and the like;

Anti-inflammatory agents such as hydrocortisone, dexamethasone, triamcinolone, prednisolone, fluorometholone, flucinolone acetate, loteprednol etabonate, and medrysone;

Non-steroidal anti-inflammatory drugs such as flurbiprofen, diclofenac sodium, ketorolac, indomethacin, and ketoprofen;

Analgesics such as lidocaine and tetracaine;

Antivirals such as ganciclovir;

Antifibrotic such as but not limited to TK (tyrosine kinase) inhibitors and or mitomycin C;

Glaucoma agents such as, but not limited to, Lanatoprost, Bimatopost, Travaprost, Timolol, Betaxalol, Dorzolamide, Brinzolamide, and Briminodine; and It is noted that, while examples listed above are described using either their branded or generic names, the present scope is contemplated to include both branded and generic active agents and active agent equivalents.

Other additional active agents can include artificial tears solutions, cellular adhesion promoters, decongestants, anticholinesterases, glaucoma agents, anti-oxidants, cataract inhibiting drugs, antiallergenics, antioxidants, anti angiogenic drugs, as well as other drugs that may be indicated for use in the eye.

Methods of making a drug delivery composition in accordance with the present technology comprise dispersing a formulation including a small molecule therapeutic agent in a polymer matrix selected to provide controlled release of an amount of the active agent to the eye. The formulation, including any of the secondary active agents or other components thereof, can be dispersed in a polymer matrix in any form that provides suitable stability and release kinetics. The forms in which the formulation is dispersed in the polymer include, without limitation, as a solid (rod, fiber and or thin film or strip) a gel, a powder, a suspension, and an emulsion. Thus, the composition can be shaped as an independent structure or can be associated with another substrate such as a coating on a contact lens and or punctual plug. Suspensions can be micro and/or nanoparticle suspensions. Similarly, the composition can be configured as a solid or semi-rigid monolith rod, a gel deposition with controlled degradation and release of the active drug. For delivery as a sub-conjunctival depot, iontophoretic structures can be included for assisting active migration of the drug into ocular tissue.

In a particular embodiment, the composition can be configured for a single use, where the polymer matrix and formulation are combined before placement and the composition or implant is removed or degrades upon exhaustion of the formulation. In an alternative embodiment, a formulation can be added to the polymer matrix after implantation, e.g. by injection. Injection can be made through overlying ocular structures (e.g. the conjunctiva in a subconjunctival implantation), or an injection port can be included that provides access to the polymer matrix.

The present technology also provides a method of treating or preventing an ocular disease. As an example, FIG. 1 is a flowchart of a method 100 of treating or preventing an ocular disease. The method includes providing an ocular composition comprising a polymer matrix comprising a thiolated hyaluronic acid moiety cross-linked to a second moiety and an antibiotic dispersed in the polymer matrix 110. The method also includes and applying the ocular composition to a surface of an eye of a subject to provide controlled release of the antibiotic to the eye 120.

In another aspect of the present disclosure, a method of treating or preventing an ocular disease can include administering a drug delivery composition to an eye of the subject, the drug delivery composition comprising a formulation including a small molecule therapeutic agent dispersed in a polymer matrix, wherein the polymer matrix provides controlled release of an amount of the small molecule therapeutic agent to the eye effective to treat or prevent an ocular indication. In another aspect, the method can further include identifying a subject that is expected to have an ocular disease or indication. In yet another aspect, the method can also include identifying a subject that is expected to have an ocular disease or indication induced, caused by, or associated with treatment of the subject. In one particular aspect, the small molecule therapeutic agent is an antimicrobial agent.

In yet another aspect, a method for treating or preventing an ocular disease or indication, and administering to the subject a topical pharmaceutical formulation having an antibiotic and optionally an additional small molecule therapeutic agent, and a pharmaceutical acceptable carrier in a polymer matrix. According to this embodiment, a subject that is likely to have a disease of the eye and/or ocular surface (e.g. cornea) is identified. In a specific aspect of this embodiment, the optional small molecule therapeutic agent can be ketorolac, naphazoline, lidocaine, pemirolast, brimonidine, bepotastine, cysteamine, difluprednate, bimatoprost, dexamethasone, unoprostone isopropyl, travoprost, valganciclovir, cidofovir, verteporfin, tafluprost, ganciclovir, or combinations thereof.

As used herein, an effective amount as it relates to treating or preventing an ocular disease or indication is an amount of the antibiotic or small molecule therapeutic agent that when applied to an ocular tissue (or location) improves the ocular disease or indication as compared to a tissue (or location) that is not treated with the therapeutic agent. In one specific aspect, the effective amount is an amount useful for treating a corneal ulcer.

In another aspect, the present disclosure additionally provides a variety of ocular inserts for the delivery of the active agent into the eye. An ocular insert is a sterile, thin, multilayered device and/or implant having a solid or semi-solid consistency configured to be placed into the cul-de-sac or conjuctival sac and/or on the surface of the bulbar conjunctiva and or cornea, whose size and shape are designed for ophthalmic application. An ocular insert is composed of a polymeric support that may or may not contain an active agent. An ocular insert can be a soluble, bioerodible, or insoluble (e.g., osmotic, diffusion, or contact lens like). The active agent can be incorporated as a dispersion or a solution in the polymeric support or any other acceptable manner (e.g., as a coating on a contact lens). An ocular insert may be configured to have a body portion sized to position within the conjunctiva cul de sac of the eyelid. A few non-limiting examples of ocular inserts can include membrane-bound ocular inserts (biodegradable and non-biodegradable), for example, Ocuserts® (Alza Corp), mucoadhesives dosage forms (ocular films or sheath, ophthaCoil, polymer rods, HEMA hydrogel, dispersion, polysulfone capillary fiber), collagen shields, cyclodextrine-based systems, ophthalmic rods (artificial tear inserts, e.g., Lacrisert®), and the like.

In one aspect, the ocular insert as described herein can include a variety of useful properties. For example, an ocular insert can be made of a bioerodible film, and thus degrades in the subject's body (e.g., eye or cul-de-sac of the eye) from about 1 to about 30 days, from about 3 to about 20 days, from about 5 to about 14 days, and in some cases from about 7 to about 10 days. Such an insert device can also release an active agent over the course of the degradation period, and is formable into various shapes, depending on the desired application. Additionally, inserts can be nonirritating to the patient, and drug released from the ocular insert remains active. The ocular insert can be produced as a sterile final product.

Various methods can be used to sterilize the ocular insert. For example, the ocular insert can be sterilized using a sterilization method that is compatible with both the polymer matrix and the antibiotic in the ocular insert. In some examples, the ocular insert can be sterilized using ethylene oxide, supercritical carbon dioxide, gamma rays, or combinations thereof.

The ocular insert, in some aspects, has a thickness which allows for use in the eye. For example, the hydrogel thickness can be from about 0.1 mm to about 5 mm thick, about 0.2 mm to about 5 mm thick, 0.3 about mm to about 5 mm thick, 0.4 about to about 5 mm thick, about 0.5 to about 4.5 mm thick, about 0.5 to about 4 mm thick, about 0.5 mm to about 3.5 mm thick, or about 0.5 to about 3 mm thick. As the skilled artisan understands, the specific dimensions of the ocular insert may vary although the size is commensurate with the specific application. A variety of shapes are contemplated herein for the ocular insert including, but not limited to, discs and threads. The insert can be of any shape and size and, preferably, is in the shape of a rod, strip, thread, doughnut, disc, oval, or quarter moon. It can be so large as to cover the entire globe of the eye or small enough to be inserted between the globe and the superior and/or inferior lid as well as against the cornea and or sub conjunctively and or subtenons. In one aspect, the ocular insert is provided as a sterile, single-dose (e.g., controlled released), ophthalmic formulation.

The ocular insert, in one embodiment, is a hydrogel comprising a hyaluronic acid moiety cross-linked to a second moiety capable of crosslinking with the hyaluronic acid moiety. In one aspect of this embodiment, the ocular insert is a hydrogel comprising a thiolated hyaluronic acid moiety cross-linked to a second moiety (e.g., compound) capable of crosslinking with the thiolated hyaluronic acid moiety. In one aspect of this embodiment the ocular insert is a hydrogel comprising a thiolated carboxymethyl hyaluronic acid cross-linked with a poly(ethylene glycol) diacrylate. In one aspect, the hydrogel is a hyaluronic acid moiety cross-linked with a polyalkylene diacrylate moiety. In one aspect, the hydrogel is a hyaluronic acid moiety cross-linked with a polyalkylene diacrylate moiety wherein the polyalkylene portion of the diacrylate is an alkylene group having from 1 to 4 carbons.

In one embodiment, the ocular insert is a hydrogel comprising a thiolated carboxymethyl hyaluronic acid cross-linked with poly(ethylene glycol) diacrylate wherein the ratio of thiol to acryl is from 1:2 to 6:1, 1:1 to 5:1, 1:1 to 4:1, or 1:1 to 3:1. In one embodiment, the ocular insert is prepared from a thiolated carboxymethyl hyaluronic acid (CMHA-S) using from about 5 to about 25, about 7 to about 22, about 10 to about 19, or about 11 to about 17 mg/ml and a second moiety which is a polyalkylene diacrylate. In another aspect, the ocular insert is a film containing thiolated carboxymethyl hyaluronic acid cross-linked with a poly (ethylene glycol) diacrylate to have from 1:2 to 4:1, 1:1 to 2.5:1 or about a 1.5:1 thiol to acryl ratio (or plus or minus 20% thiol or diacrylate). The ocular insert can also contain from about 1 mg/mL to about 50 mg/mL or 10 mg/mL (or plus or minus 50%) methylcellulose (MC). The MC provides some flexibility to the films and renders them somewhat mucoadhesive. Hyaluronic acid and derivatives thereof can form hydrogels with a variety of molecules including, but not limited to, dithiobis(propanoic dihydrazide) (DTP), dithiobis(butyric dihydrazide), and the like.

Hyaluronic acid and derivatives thereof can form hydrogels with a variety of other molecules by crosslinking with a poly(ethylene glycol) diepoxide group. The hydrogel may further include other agents. One example of such agents is a mucoadhesive and/or flexibility improving agent e.g., methylcellulose. The other agents in the hydrogel are chosen such that they do not prevent formation of the hydrogel or release of the drug from the hydrogel. Agents that can improve flexibility and/or mucoadhesiveness of the ocular insert are known to the skilled artisan.

As described herein, the present technology provides an ocular insert comprising a small molecule therapeutic agent. In some embodiments, the ocular insert can have a small molecule therapeutic agent incorporated into the hydrogel at from about 0.01 to about 50, or about 1 to about 27 mg/mL.

The topical ocular pharmaceutical compositions can include a topical ocular carrier and an effective amount of a small molecule therapeutic agent. The pharmaceutical compositions described herein may comprise a carrier suitable for intraocular administration, such as, for example, Ringer's solution or balanced salt solution, and an effective amount of a pharmaceutically acceptable a small molecule therapeutic agent. The carrier for intraocular pharmaceutical compositions can be free of microbes and endotoxins. Topical ocular formulations provided herein are configured for application to the eye. In some embodiments, the topical ocular formulation is in the form of ocular inserts, eye drops, eye washes, contact lens solutions, ointments, gels, patches, packs, depot formulations, sustained or continued release formulations, aerosols, and the like. In various embodiments, the topical ocular formulation is provided in single or multi-dose containers or dispensers. The disclosure also provides intraocular formulations in the form of injectable solutions, eye irrigating solutions, volume replacement solutions, films, gels, depot formulations, slow release formulations, and the like. In various embodiments, the intraocular formulation may be provided in single or multi-dose containers or dispensers, or in implantable intraocular devices.

An article of manufacture is also provided herein. According to one embodiment, the article of manufacturer comprises a vessel containing a composition or formulation as described herein and instructions for use for the treatment of a subject. For example, an article of manufacture, comprising a vessel containing a formulation configured for topical application to the eye and instructions for use for the treatment of a subject suffering from an ocular disease or indication.

In the present description, the terms "topical" and "topical application" refer to the non-systemical administration of the active ingredient to an external surface for local effect (e.g., of the wound or close to the wound or target ocular region or tissue). Preferably the composition is sterile or aseptic and can be packaged in tubes, bottles or other containers suitable for easy topical application.

EXAMPLES

The following examples are included to illustrate concepts and particular embodiments related to the invention. As will be appreciated by those of skill in the art, the techniques, methods and compositions disclosed in the following examples are representative of particular modes for practice of the invention while not being intended to limit scope of the invention.

Example 1: Preparation of Polymer Topical Formulation

A quantity of ten HYSTEM-LS vial (20 mg) {thiolated hyaluronate (e.g., thiolated carboxymethyl hyaluronic acid)} were stored at −20 deg C. for long term storage and kept at room temperature for no more than 12 hours. One vial was resuspended each day and used as stock for that day. Five lactated ringers 10 ml vials were stored at room temp, or long term storage at 4 deg C. Two vials of 20 mM acrylate derivatized PEG (PEGDA) in Lactated Ringers (0.0656 g in 5 ml Lactated Ringers) (Sigma-Aldrich catalog number: G4626) were stored powder at −20 deg C.; store resuspended solutions at −20 deg C. These are resuspended and aliquoted out on surgery day.

To the tube filled with PEGDA powder, the top of lactated ringers vial was swabbed with an alcohol wipe and 5 ml Lactated Ringers solution was withdrawn. An amount of 5.0 ml was added to the PEGDA tube and vortex well was used to resuspend until all powder was dissolved. A 0.2 micron syringe filter was affixed to a 5.0 ml syringe with its plunger pulled out. With the syringe filter still in its container, the syringe was filled with 5 ml PEGDA solution. Using the plunger, filter sterilized into a fresh sterile 15 ml falcon tube and the tube was recapped. The solution was aliquot into sterile eppendorf tubes: 50 ul/tube, 20 tubes (this is for the HYSTEM/PEGDA administrations), 125 ul/tube, 20 tubes (this is for the HYSTEM/PEGDA/Active Agent administrations), and tubes labeled as "50 ul" or "125 ul" and place all tubes at −20 deg. C. for the week.

One HYSTEM-LS vial and lactated ringer was sterilized. A sterile syringe was used to withdraw 2 ml Lactated Ringers Solution and inject into the HYSTEM-LS vial and pellets were agitated until completely hydrated. Mechanical agitation was performed by hand and by rotary shaker (150 rpm with tube on side) until the pellets were completely dissolved (up to 45 min or until all translucent chunks were dissolved).

An amount of 20× stock (800 ug/ml) was prepared for HYSTEM-LS/PEGDA mixture. The mixture was resuspend gently by swirling tube by hand in 2.5 ml Lactated Ringers and place at 4 deg. C. for the day. (2.5 ml total volume).

HYSTEM-LS/PEGDA/Active Agent application was accomplished by thaw a "125 ul" PEGDA tube using hands. An amount of 469 ul of HYSTEM-LS was added to the PEGDA tube and mixed. An amount of 31 ul 20× Active Agent stock was added and mixed gently by upending well by hand (no vortexing). Gelation occurred in about 10 minutes at room temperature. A sterile P200 tip was used to aspirate 50 microliters of the mixture and gently dispense onto the surface of the 10 rabbit eyes randomized to the test HYSTEM/Active Agent group. The rabbits eye were coated completely.

Example 2: Drug Releasing Hydrogel Film

This example describes the preparation of a drug-releasing hydrogel film that is useful for treating conditions of the eye and especially those conditions described herein. The hydrogel is based on thiolated carboxymethyl hyaluronic acid (CMHA-S), supplied by BioTime, Inc. (Alameda, Calif.). The hydrogel is formed by crosslinking the CMHA-S with poly(ethylene glycol) diacrylate (PEGDA), also supplied by BioTime. The film is created by drying the hydrogel after incorporating the small molecule therapeutic agent.

CMHA-S was dissolved in varying amount of water depending on the final HA concentration. The tube was placed on an orbital shaker in a 37° C. incubator. The tube was repeatedly vortexed every 15-30 minutes until CMHA-S was fully dissolved. PEGDA was placed in a separate centrifuge tube. PBS was added to this tube, and then the tube was vortexed to mix. A volume of 100 mg/ml MC (methylcellulose) was added to the CMHA-S solution. This mixture was mixed gently by inversion. The PEGDA solution was then transferred into the CMHA-S/MC solution, and the mixture was mixed by inversion. This final solution was aliquotted into prepared wells and a silicon mold. Adequate crosslinking occurred when the final solution no longer flowed when the tube was inverted, which occurred within 15-30 minutes. The hydrogels were allowed to sit at room temperature for a total of 2 hrs (from the time of aliquoting). The hydrogels were transferred to an oven (37° C.), for 12-24 hrs to dry the films. The films were removed from the oven and allowed to equilibrate to room temperature for 1-2 hrs. The films were then removed from the wells and mold.

Films were made in two ways: 1) In a 5 cm×5 cm×2 mm silicone mold (5 mL volume); and 2) In 12-well MicroFlex-iPerms placed on an acrylic sheet, using enough solution for the films to be ~3 mm thick.

For each method, two concentrations of CMHA-S were used—either 12 mg/mL or 16 mg/mL. These films contained enough PEGDA to have a 1.5:1 thiol to acrylate ratio, and also contained 10 mg/mL methylcellulose (MC). The MC provides some flexibility to the films and renders them somewhat mucoadhesive. Disks (6 mm diameter) were punched out of films made using method 1, using a standard hole punch. Thus, 4 film types were created, all ~6 mm in diameter—12 mg/mL CMHA-S with a thickness of 2 mm; 12 mg/mL CMHA-S with a thickness of 3 mm; 16 mg/mL CMHA-S with a thickness of 2 mm; and 16 mg/mL CMHA-S with a thickness of 3 mm.

Example 3: HA Film Formation

Films were formed with a final concentration of 16 mg/mL CMHA-S and a final concentration of 5 mg/mL MC. An amount of 80 mg of CMHA-S were dissolved in 2 mL of PBS. 25 mg of methyl cellulose (MC) was also dissolved in 2 mL PBS. The CMHA-S solution was mixed with the MC solution. The total volume was 4 mL. While waiting for CMHA-S/MC solution to be completely dissolved, 57 mg of polyethyleneglycol diacrylate (PEGDA) was dissolved in 1 mL PBS. A specific amount of moxifloxacin (5 mg for the well mold, 8 mg for the square mold) was added to PEGDA solution. The final concentration of moxifloxacin was 100 mg per film. Next, the CMHA-S/MC solution was mixed with the PEGDA/moxifloxacin solution. This final solution had a 1.5:1 thiol to acrylate ratio and 5 mL final volume. The final mixed solution was used for casting a gel. For casting the gel, two different molds were used: 1) a well-mold (6 mm wells), each well having 100 µL of the final solution transferred therein; and 2) a square mold (5 cm×4.5 cm), into which 5 mL of the final solution was poured.

After 15 min of gelation and an hour of incubation at room temperature, the molds were transferred to an oven at 37 C. After 18 hour of drying in the oven and an hour of sitting at room temperature, the film was removed from the well-mold. For the square mold, a punch (6 mm diameter) was used to cut 6 mm diameter films.

The film was transferred to 250 µL PBS buffer for the antibiotic release study. On each day, 200 µL of PBS was pulled off, and 200 µL of fresh PBS was added to the tube until day 7. UV absorbance was measured at 293 nM, and the released amount of antibiotic was calculated from the standard curve.

Figure 2:
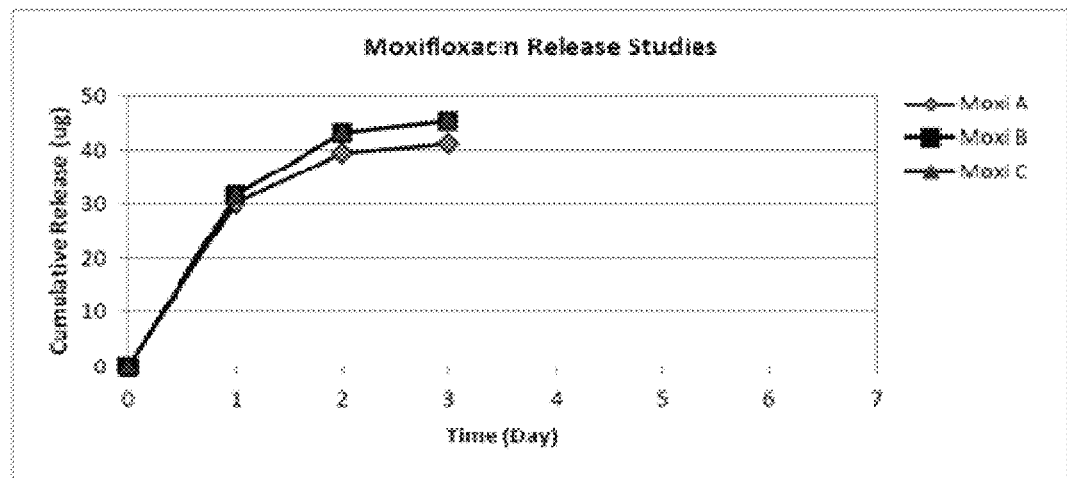
FIG. 2 shows cumulative antibiotic release for ocular compositions in accordance with an embodiment of the present disclosure.

FIG. 2 shows the cumulative antibiotic release for films (made from CMHA-S and PEGDA) that had three different thiol to acrylate ratios: A (1.5), B (2.0), and C (2.5). Moxifloxacin (150 µg/film) was used for this study. The accumulated released amount of moxifloxacin is more than 40 µg (thus about 27% release) at Day 3. In FIG. 2, although it may not be apparent, the Moxi B and Moxi C data points are superimposed on one another.

Figure 3:
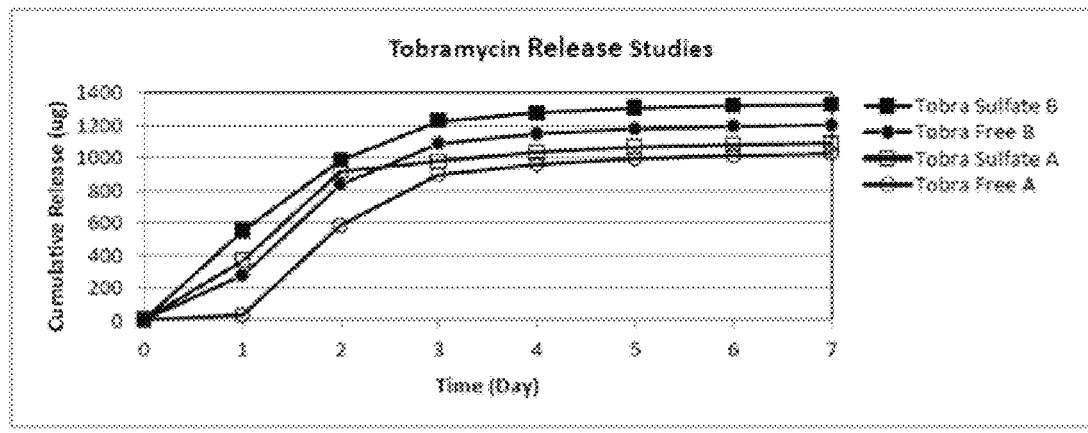
FIG. 3 shows cumulative antibiotic release for ocular compositions in accordance with an embodiment of the present disclosure.

As shown in FIG. 3, films (made from CMHA-S and PEGDA) were made with two different thiol to acrylate ratios: A (1.5) and B (2.0). Tobramycin sulfate (2 mg/film) and tobramycin free base (2 mg/film) were used for this study. As tobramycin absorbs UV weakly, OPA assay and measuring fluorescence were used to calculate cumulative release of tobramycin. Amount of release tobramycin was calculated from standard curve. The accumulated release amount of tobramycin was more than 1 mg (thus more than 50% release) over 7 days.

These studies show that small molecule therapeutics can be released continuously (e.g., including in a sustained release fashion) from the ocular composition as described herein for at least 1 day, at least 2 days, and at least 3 days or more.

Example 4: HA Film Formation 2

Films were formed with a final concentration of 16 mg/mL CMHA-S and 5 mg/mL MC. An amount of 80 mg of thiolated carboxymethyl hyaluronic acid (CMHA-S) were dissolved in 2 mL of PBS. 25 mg of methyl cellulose (MC) were also dissolved in 2 mL PBS. The CMHA-S solution was mixed with MC solution. The total volume was 4 mL. While waiting for the CMHA-S/MC solution to completely dissolve, 57 mg of polyethyleneglycol diacrylate (PEGDA) were dissolved in 1 mL PBS. A specific amount of ketorolac (5 mg for the well mold, 8 mg for the square mold) was added to the PEGDA solution. The final concentration of ketorolac was 100 µg per film. Next, the CMHA-S/MC solution was mixed with the PEGDA/ketorolac solution. The resulting solution had a 1.5:1 thiol to acrylate ratio and the final volume was 5 mL. The final mixed solution was used for casting a gel. For casting the gel, two different molds were used: 1) a well-mold (6 mm wells), in which each well contained 100 µL of the final solution; and 2) a square mold (5 cm×4.5 cm), into which five mL of the final solution was poured.

After 15 min of gelation and an hour of incubation at room temperature, the molds were transferred to an oven at 37° C. After 18 hours of drying in the oven and an hour of sitting at room temperature, the films were removed from the well-mold. For the square mold, a punch (6 mm diameter) was used to cut 6 mm diameter films.

The films were transferred to 250 µL PBS buffer for the ketorolac release study. On each day, 200 µL of PBS were pulled off, and 200 µL of fresh PBS were added to the tube until day 7. The amount of ketorolac released was determined using standard methodologies or adaptations thereof.

Example 5: HA Film Formation 3

Films are formed with a final concentration of 16 mg/mL CMHA-S and 5 mg/mL MC. An amount of 80 mg of thiolated carboxymethyl hyaluronic acid (CMHA-S) are dissolved in 2 mL of PBS. 25 mg of methyl cellulose (MC) are also dissolved in 2 mL PBS. The CMHA-S solution is mixed with the MC solution for a total volume of 4 mL. While waiting for CMHA-S/MC solution to completely dissolve, 57 mg of polyethyleneglycol diacrylate (PEGDA) can be dissolved in 1 mL PBS. A specific amount of ganciclovir (5 mg for the well mold, 8 mg for the square mold) is added to PEGDA solution. The final concentration of ganciclovir is 100 mg per film. Next, the CMHA-S/MC solution is mixed with the PEGDA/ganciclovir solution. The resulting solution has a 1.5:1 thiol to acrylate ratio and a final volume of 5 mL. The final mixed solution is used for casting a gel. For casting the gel, two different molds are used: 1) a well-mold (6 mm well) in which each well contains 100 μL of the final solution; and 2) a square mold (5 cm×4.5 cm) into which 5 mL of the final solution is poured.

After 15 min of gelation and an hour of incubation at room temperature, the molds are transferred to an oven at 37° C. After 18 hours of drying in the oven and an hour of sitting at room temperature, the films are removed from the well-mold. For the square mold, a punch (6 mm diameter) is used to cut 6 mm diameter films. The films are transferred to 250 μL PBS buffer for the ganciclovir release study. On each day, 200 μL of PBS are pulled off, and 200 μL of fresh PBS are added to the tube until day 7. The amount of ganciclovir released is determined using standard methodologies or adaptations thereof.

Example 6: HA Film Formation 4

Films are formed with a final concentration of 16 mg/mL CMHA-S and 5 mg/mL MC. An amount of 80 mg of thiolated carboxymethyl hyaluronic acid (CMHA-S) is dissolved in 2 mL of PBS. 25 mg of methyl cellulose (MC) is also dissolved in 2 mL PBS. The CMHA-S solution is mixed with the MC solution for a total volume of 4 mL. While waiting for CMHA-S/MC solution to completely dissolve, 57 mg of polyethyleneglycol diacrylate (PEGDA) is dissolved in 1 mL PBS. A specific amount of latanoprost (5 mg for the well mold, 8 mg for the square mold) is added to the PEGDA solution. The final concentration of latanoprost is 100 mg per film. Next, the CMHA-S/MC solution is mixed with the PEGDA/latanoprost solution. The resulting solution is a 1.5:1 thiol to acrylate ratio and a final volume of 5 mL. The final mixed solution is used for casting a gel. For casting the gel, two different molds are used: 1) a well-mold (6 mm well) in which each well contain 100 μL of the final solution; and 2) a square mold (5 cm×4.5 cm) into which 5 mL of the final solution is poured.

After 15 min of gelation and an hour of incubation at room temperature, the molds are transferred to an oven at 37° C. After 18 hour of drying in the oven and an hour of sitting at room temperature, the films are removed from the well-mold. For the square mold, a punch (6 mm diameter) is used to cut 6 mm diameter films. The films are transferred to 250 μL PBS buffer for the latanoprost release study. On each day, 200 μL of PBS are pulled off, and 200 μL of fresh PBS are added to the tube until day 7. The amount of latanoprost released is determined using standard methodologies or adaptations thereof.

Example 7: Film Formation and Swelling

Films were formed with a final concentration of 16 mg/mL CMHA-S. After mixing the CMHA-S (Glycosil® from BioTime, Inc.) and PEGDA, the mixed solution was cast in either acrylic/silicone molds (acrylic bottom and silicone sides) or silicone molds (silicone bottom and sides). After 2 hour of incubation at room temperature, the hydrogels were placed in the oven for 18 hours to be dried. In order to manufacture multiple numbers of films, the square molds (5.0 cm L×5.0 cm W×1 mm H) were used, and after drying, individual films was created by cutting with a 6 mm hole-punch. A 12-well mold was utilized for in vitro studies, while the square mold was utilized for in vivo studies. For cutting small films out of a larger sheet, the 6 mm hole punch method was utilized and the cut edges were smooth and even.

The concentrations of CMHA-S and PEGDA provided a 1.5:1 molar ratio of thiol to acrylate groups. Diameter and mass of the 6 mm diameter dry films cut from larger films was determined. Films were then placed in simulated tear fluid (STF; 2.68 g/L BSA, 1.34 g/L globulin, 0.08 g/L CaCl2, 6.58 g/L NaCl, 6.5 g/L glucose, 2.68 g/L lysozyme). The films were allowed to swell in the STF, and diameter and mass of the reswollen films were determined. Films were also placed in STF with 0, 50, or 100 U/ml bacterial hyaluronidase (HAase), representing normal tear fluid and fluid from eyes with moderate and severe bacterial infections. Film degradation over 4 days was assessed by removing the fluid on a daily basis and replacing it with fresh STF/enzyme solution. The removed fluid was assayed for uronic acid released from the breakdown of Glycosil by HAase using a carbazole assay.

Figure 4:
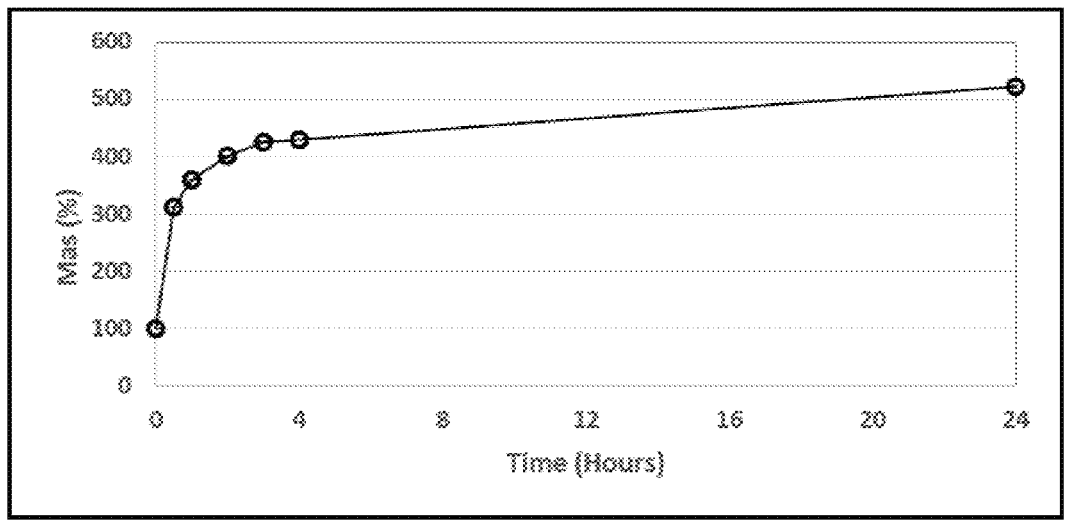
FIG. 4 shows increase of mass percentile of swelling films in simulated tear fluid in accordance with an embodiment of the present disclosure.

FIG. 4 shows the increase in mass percent of the films as the films swelled in the STF solution. By 4 hours, the films had swollen more than 400%. At 24 hours, the films had swollen approximately 500%. The diameter of the films increased from 6 mm to 8 mm within the first 20 minutes and remained unchanged thereafter.

Example 8: Film Degradation

Figure 5:
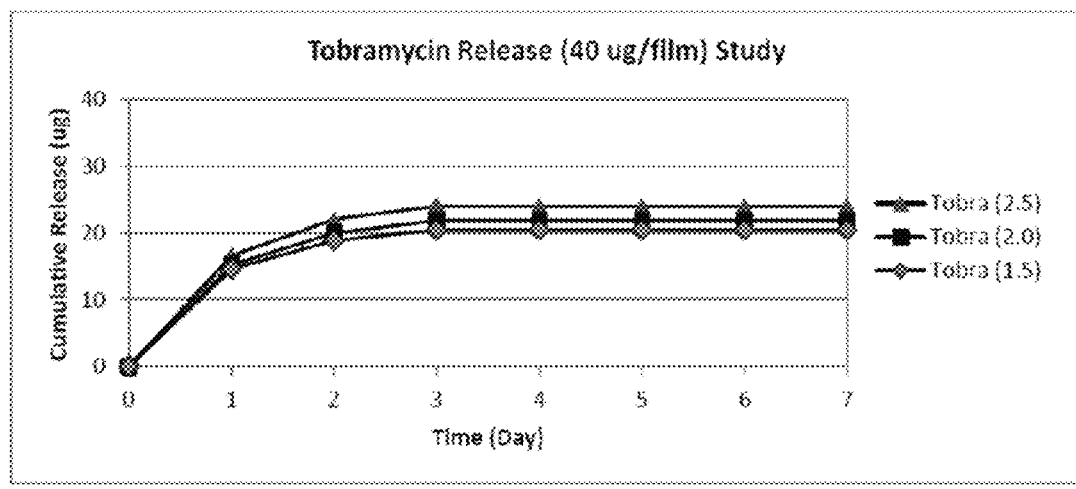
FIG. 5 shows cumulative antibiotic release for ocular compositions in accordance with an embodiment of the present disclosure.

HA film degradation was assessed in STF, 50 U/ml HAase, and 100 U/ml HAase for five days. For this study, HA films were prepared in three different HA concentrations; 10%, 12%, and 16%. Thus, three variables were used in this study; media, time, and HA concentration. Daily removed fluid was assessed for degradation by measuring the amount of uronic acid by carbazole assay (FIG. 5). At day 1, in STF, no uronic acid was detected, which suggests the film did not degrade. The film remained intact no matter what CMHA-S concentration was used. In 50 U/ml HAase, the film degraded, and generated roughly 7 mg of uronic acid. The degradation extent was similar for the different concentrations of HA. In 100 U/ml HAase, the film generated roughly 9 mg of uronic acid. The degradation extent again was similar for each different concentration of CMHA-S. The carbazole assays were continued for 4 days. Only negligible levels of uronic acid were detected after day 2 and beyond for all films. For STF, the film remained intact, thus no uronic acid was detected (no blue bar). With either concentration of HAase, the films began to degrade as early as day 1, thus no uronic acid was detected beyond 24 hours.

Example 9: Antibiotic Release, Sterilization, and Efficacy

Films were formed with a final concentration of 16 mg/mL CMHA-S. The concentration of PEGDA provided a 1.5:1, 2:1, or 2.5:1 molar ratio of thiol to acrylate groups in order to vary the degree of crosslinking. The films also contained either tobramycin or moxifloxacin. For the tobramycin-containing films, the antibiotic was added to the CMHA-S solution prior to mixing with the PEGDA solution. Initially, a concentration of tobramycin of 10 mg/mL was used as this would provide 0.75 mg tobramycin in a 6 mm film. This falls between the approved and marketed dose of 3 mg/mL used in topical drops and the increased compounded concentration of 15 mg/mL that is the accepted dose needed for corneal ulcers.

For the moxifloxacin-containing films, dosing was based on the approved dose of 5 mg/mL administered as a 40 µL drop 24 times a day for a corneal ulcer. Here, the moxifloxacin and the CMHA-S were dissolved in 0.5×PBS prior to adding the PEGDA solution. The following variables were also altered and modified to assess their effect on in vitro release: PEGDA crosslinking ratios, amount of HA, free base vs salt, order of solubilization of the film components, release media (PBS vs STF), and the volume of release buffer.

Drug-loaded films were placed in PBS for the antibiotic release study. The fluid was removed and assayed daily. For tobramycin, detection was performed using an O-phthaldialdehyde (OPA) reagent. OPA, in the presence of reduced sulfhydryl groups, reacts with the primary amine group in tobramycin to form fluorescent moieties. The fluorescence was measured at an excitation wavelength of 360 nm, and an emission wavelength of 460 nm. The amount of released drug was calculated using a standard solution of tobramycin. For moxifloxacin, UV absorption at 293 nm was used to measure the amount of released drug. The amount of released drug was calculated using a standard solution of moxifloxacin. This removed fluid was also used to assess the bactericidal capability of released antibiotic by the disk diffusion method on agar plates seeded with S. aureus and P. aeruginosa measuring zone of inhibition (ZOI). Similar ZOI bacterial work was also performed using the actual films by an outside lab, Analytical Resource Lab (ARL, Salt Lake City, Utah).

In order to identify viable sterilization techniques that would be compatible with both the CMHA-S film and the antibiotic, disks were made as above both with and without antibiotic. Films were sterilized by the following three methods: EtO (at SentrX Animal Care), supercritical CO2 (at NovaSterilis), and gamma irradiation (25 kGy). Following sterilization, drug release profiles and bactericidal capability were assessed as described above and compared to the films that had not been sterilized.

FIG. 5 shows cumulative release of tobramycin from films with 3 different thiol to acrylate ratios: 1.5, 2.0, and 2.5. Each film contained 40 µg of tobramycin free base. CMHA-S films were made with 3 different crosslinking ratios: 1.5, 2.0, or 2.5. As tobramycin absorbs UV weakly, OPA assay was used to measure fluorescence using low concentrations of tobramycin. The amount of released tobramycin was calculated from a standard curve. The accumulated released amount of tobramycin was more than 20 µg (thus more than 50% release) over 7 days. The release increased continuously up to day 3 and remained unchanged for the different thiol to acrylate ratios.

Figure 6:
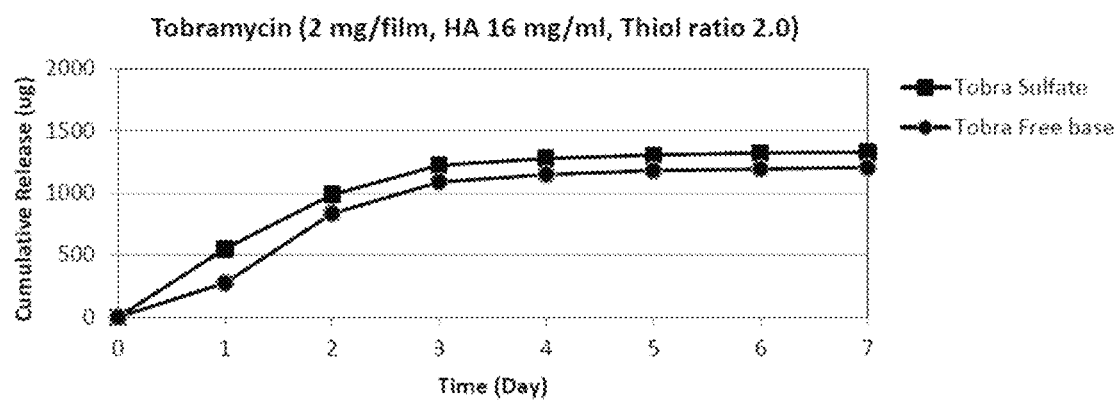
FIG. 6 shows cumulative antibiotic release for ocular compositions in accordance with an embodiment of the present disclosure.

FIG. 6 shows cumulative release of tobramycin from films containing 2 mg of tobramycin sulfate or tobramycin free base. The films had a concentration of CMHA-S of 16 mg/mL and a thiol to acrylate ratio of 2.0. Additionally, the order of combining the drug with PEGDA before mixing with CMHA-S was changed to combine the drug with CMHA-S first, then combining the mixture with PEGDA. These changes did not have an appreciable effect on the release profile.

Figure 7:
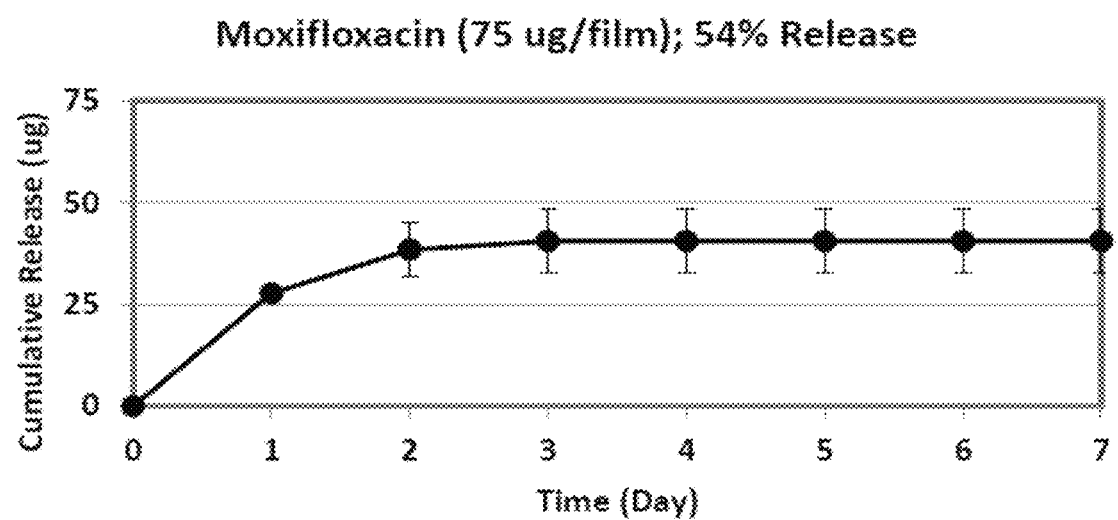
FIG. 7 shows cumulative antibiotic release for ocular compositions in accordance with an embodiment of the present disclosure.

FIG. 7 shows cumulative release of moxifloxacin from films in PBS. The films contained 75 µg of moxifloxacin, of which 40.5 µg were released over 7 days. The films had a thiol to acrylate ratio of 1.5. The films were placed in PBS, and the released moxifloxacin was monitored every day by measuring UV at 293 nm. The amount of released moxifloxacin was calculated from the standard curve. The assay was performed in triplicate. Fifty four percent of moxifloxacin was released through day 3. The drug release was also evaluated using STF instead of PBS, and the release profile again remained unchanged.

To assess bactericidal capability of released antibiotics, zone of inhibition (ZOI) tests were performed. ZOI plates were seeded with S. aureus 49230, the samples were loaded (in triplicate, thus three plates), and the plates were incubated overnight. The ZOI was measured on the following day. In each plate, pre-sterilized films and post-sterilized films containing moxifloxacin were loaded. ZOI was measured for the films and a moxifloxacin standard solution, and the amount of drug was calculated from the standard curve. After EtO sterilization, the efficacy of moxifloxacin remained the same or reduced to 90% depending on the bacterial strain. The same experiment was repeated for CO2 and gamma sterilizations, and the efficacy of moxifloxacin was compared with the pre-sterilized sample. Specifically, the film with EtO sterilization had 103.2% efficacy (compared with the moxifloxacin standard solution) against S. aureus and 90.2% efficacy against P. aeruginosa; the film with CO2 sterilization had 75.7% efficacy against S. aureus and 96.2% efficacy against P. aeruginosa; and the film with gamma sterilization had 43.9% efficacy against S. aureus and 68.8% efficacy against P. aeruginosa. EtO sterilization showed the best compatibility with the film and drug thus not affecting drug release and or drug efficacy (efficacy remained at >90%).

For the ZOI studies, the amount of drug released was measured using a 96-well plate reader, where the lowest concentration that could be detected was 10 µg/ml. The amount of efficacious drug released was consistent up through day 3 based on bacterial inhibition through day 3 and was 70 µg in total. No drug release was detected on day 4 or beyond, which may be result of insufficient sensitivity in detecting drug.

Example 10: In Vivo Testing

The films as described above were tested for in vivo use in an eye. The antibiotic-containing HA films can be safely and easily placed in a rabbit eye cul de sac, remain in this location adjacent to the bulbar conjunctiva, and be well-tolerated while releasing antibiotics locally for up to 7 days. Films with two different doses (30 µg/film and 100 µg/film) of moxifloxacin were used to assess tolerability over an acceptable dose range.

Rabbits (Species: *Oryctolagus cuniculus*; Strain: New Zealand White rabbits; Sex: Female & Male; Age: Commensurate with weight; Weight: 2.8 to 3.4 kg; Number: 24; Minimum Acclimation: 5 days) were used for in vivo testing. Prior to placement on study, each animal underwent a complete ophthalmic examination (by slit lamp biomicroscopy with fluorescein staining, indirect ophthalmoscopy). Ocular findings were scored according to the standard non-invasive McDonald Schadduck Score System. The acceptance criteria for placement on study were scores of "0" for all variables.

Experiments were conducted in accordance with the ARVO Statement for the Use of Animals in Ophthalmic and Vision Research, and were approved by the AS Institutional Animal Care and Use Committee. Due to the ability of the rabbit's nictitating membrane and/or third eyelid to physically push out the HA films, the nictitating membrane of each rabbit eye was removed prior to film placement without complications. The eyes were allowed to heal for at least 2 weeks.

Ocular placement of the HA films occurred 2 weeks post-surgical removal of the nictitating membrane. The animals were restrained manually, the lower lid was protracted, and the bulbar and palpebral conjunctival tissue dried. One film/designated eye, was wetted with balanced saline solution (BSS) and placed on the surface of the bulbar conjunctival in the inferior cul de sac, and the lid was allowed to return. Each right eye (OD) received one of the 2 doses of the antibiotic-containing film, while the left eye (OS) served as the control and received no treatment or received a film without antibiotic, ensuring that at each time point there were 3 eyes with each treatment being evaluated. Thus, the 4 treatment arms (n=24 rabbits (48 eyes)) were: Low dose (30 μg) antibiotic-containing film (OD); High dose (100 μg) antibiotic-containing film (OD); Film alone (no antibiotic) (OS); and Untreated control eye (OS).

Safety, biocompatibility and feasibility were evaluated at four points post-implantation (Day 0) on Days 1, 3, 4, and 7. At each of these four time points, all rabbits had clinical ophthalmic examinations, including slit lamp biomicroscopy with photography. The presence and appearance of the polymer in each eye was photographed and noted. The exams were used to determine tolerability (Draize score) as well as the product presence and stability of the film on the inferior ocular bulbar conjunctival surface. The film (if present) was removed from 3 eyes/arm (total of 6 rabbits/time point) at each time point and tested to determine the amount of degradation and remaining amount of drug. Digital photographs were taken of the polymer product in the eye at each slit lamp examination using a Haag-Streit BP 900 Slit Lamp in order to document location in all rabbits. On days 1, 2, and 3, 5-20 μL of tears was collected from the right eyes of rabbits containing the active drug films. At three of the scheduled time points, the six animals (i.e., 3 eyes/arm) from which the polymer had been removed (or was not present) were euthanized and necropsy preformed. Of note, no films remained in the eyes at Day 7. The eyes were enucleated and all globes trimmed and processed.

The data generated in vivo confirmed excellent safety and tolerability of the films—both drug-loaded and blank controls—over the course of 7 days (scores of 0 to 1 on Draize). In terms of film retention, the location and retention in the inferior cul de sac was excellent on days 1 and 2. On day 3, however, 100% of the films had moved nasally towards the medial canthus. By day 4, three rabbits had dislodged films, which were then replaced inferiorly. No films were present in the eyes on day 7. Some of the films had either broken and or dislodged during the study. Upon daily exams, if it was found that films had moved, they were either replaced into the cul de sac at each exam and/or removed prior to sacrifice.

Figure 8:
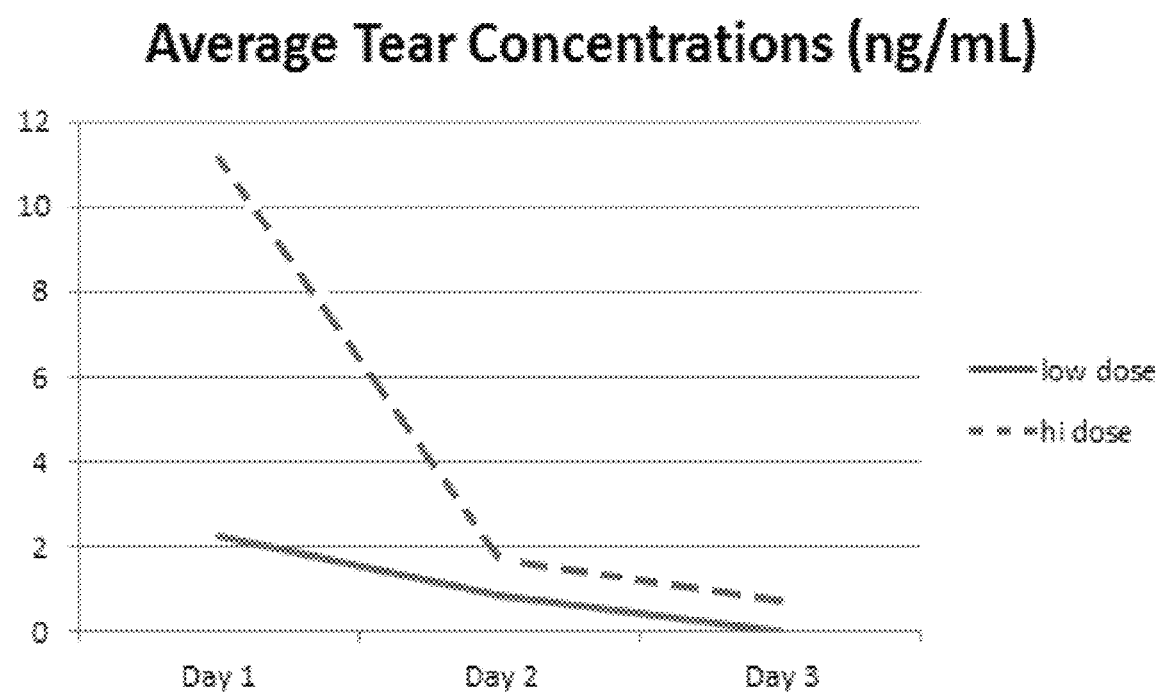
FIG. 8 shows average tear concentrations of antibiotic in rabbits treated with one initial application of the ocular compositions in accordance with an embodiment of the present disclosure.

Collected tears were tested for antibiotic concentration. FIG. 8 shows the average tear concentrations of moxifloxacin over the first three days in the low dose (30 μg) and high dose (100 μg) rabbits.

While the examples and details described above are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

What is claimed is:

1. An ocular composition, comprising:
   a polymer matrix comprising a thiolated hyaluronic acid moiety cross-linked to a second moiety, wherein the second moiety is a poly(ethylene glycol) diacrylate moiety; and
   an antimicrobial dispersed in the polymer matrix at a dosage sufficient to inhibit microbial growth;
   wherein the composition is configured for placement in or on an eye of a subject, and wherein the composition provides controlled release of from 0.5 μg to 50 μg per day of the antimicrobial to the eye over a period of from 1 week to 8 weeks.

2. The ocular composition of claim 1, wherein the composition is formulated as an ocular insert, an implantable depot, a topical formulation, a spray formulation, an injectable fluid, a microparticle suspension, a nanoparticle suspension, a monolithic rod, a film, a gel, a sponge, or a combination thereof.

3. The ocular composition of claim 1, wherein the ocular composition is formulated as a film for placement on a surface of the eye.

4. The ocular composition of claim 3, wherein the film contains from about 30 μg to about 500 μg of the antimicrobial.

5. The ocular composition of claim 3, wherein the film has a diameter from about 2 mm to about 16 mm and a thickness from about 0.05 mm to about 3 mm.

6. The ocular composition of claim 1, wherein the antimicrobial is incorporated into the thiolated hyaluronic acid moiety and second moiety before cross-linking, such that the antimicrobial is trapped within the polymer matrix after cross-linking.

7. The ocular composition of claim 1, wherein the second moiety comprises a cross-linking group capable of cross-linking with a thiol group of the thiolated hyaluronic acid moiety, and wherein the thiolated hyaluronic acid moiety and second moiety are present in amounts such that a ratio of thiol groups to cross-linking groups is from 1:1 to 2.5:1.

8. The ocular composition of claim 1, further comprising an antiviral, antifungal, anti-inflammatory steroid, non-steroidal anti-inflammatory, analgesic, artificial tears solution, decongestant, anticholinesterase, glaucoma hypotensive agent, antiangiogenesis agent, antiallergenic, anti-cancer agent or any combination thereof dispersed in the polymer matrix.

9. The ocular composition of claim 1, wherein the polymer matrix comprises a bioerodible polymer that erodes to provide a rate of controlled release.

10. The ocular composition of claim 1, wherein the polymer matrix further comprises at least one monomer selected from the group consisting of glycolic acid, glycolide, lactic acid, lactide, e-caprolactone, p-dioxane, p-diozanone, trimethlyenecarbonate, bischloroformate, ethylene glycol, bis(p-carboxyphenoxy) propane, sebacic acid, and combinations thereof.

11. The ocular composition of claim 1, wherein the thiolated hyaluronic acid moiety is a thiolated carboxymethyl hyaluronic acid moiety.

12. The ocular composition of claim 1, wherein the antimicrobial is an antibiotic and the antibiotic is selected from the group consisting of aminoglycosides, penicillins, cephalosporins, fluoroquinolones, macrolides, and combinations thereof.

13. The ocular composition of claim 12, wherein the antibiotic is an aminoglycoside selected from the group consisting of tobramycin, kanamycin A, amikacin, dibekacin, gentamicin, sisomicin, netilmicin, neomycin B, neomycin C, neomycin E, streptomycin, and combinations thereof.

14. The ocular composition of claim 12, wherein the antibiotic is at least one of tobramycin and vancomycin.

15. The ocular composition of claim 12, wherein the antibiotic is a fluoroquinolone selected from the group consisting of ciprofloxacin, levofloxacin, gatifloxacin, moxifloxacin, ofloxacin, norfloxacin, and combinations thereof.

16. The ocular composition of claim 12, wherein the antibiotic is moxifloxacin.

17. The ocular composition of claim 1, wherein the antimicrobial has a concentration in the polymer matrix from about 1 µg to about 27 µg per milliliter.

18. The ocular composition of claim 1, wherein the antimicrobial is an antifungal.

19. The ocular composition of claim 1, wherein the antimicrobial is an antiviral.

20. The ocular composition of claim 1, wherein the controlled release is over a period of from 1 week to 2 weeks.

21. A method of treating or preventing an ocular disease, comprising:
providing an ocular composition comprising:
a polymer matrix comprising a thiolated hyaluronic acid moiety cross-linked to a second moiety, wherein the second moiety is a poly(ethylene glycol) diacrylate moiety; and
an antimicrobial dispersed in the polymer matrix at a dosage sufficient to inhibit microbial growth; and
applying the ocular composition to a surface of an eye of a subject to provide a controlled release of from 0.5 µg to 50 µg per day the antimicrobial to the eye over a period of from 1 week to 8 weeks.

22. The method of claim 21, wherein the antimicrobial is released continuously.

23. The method of claim 21, wherein applying the ocular composition to the eye comprises placing the ocular composition under a contact lens or bandage lens worn in the eye.

24. The method of claim 21, wherein the ocular composition is an ocular insert, solution, film, or gel.

* * * * *